(12) United States Patent
Dixon et al.

(10) Patent No.: US 7,722,948 B2
(45) Date of Patent: May 25, 2010

(54) LAMINATED GLAZING

(75) Inventors: Jonathan Barclay Dixon, Parbold (GB); Michael Robert Greenall, Clayton-le-Woods (GB)

(73) Assignee: Pilkington Group Limited, St. Helens (GB)

( * ) Notice: Subject to any disclaimer, the term of this patent is extended or adjusted under 35 U.S.C. 154(b) by 0 days.

(21) Appl. No.: 12/083,158

(22) PCT Filed: Oct. 5, 2006

(86) PCT No.: PCT/GB2006/003717

§ 371 (c)(1),
(2), (4) Date: May 30, 2008

(87) PCT Pub. No.: WO2007/039751

PCT Pub. Date: Apr. 12, 2007

(65) Prior Publication Data

US 2009/0169877 A1    Jul. 2, 2009

(30) Foreign Application Priority Data

Oct. 6, 2005    (GB) ................................. 0520303.9

(51) Int. Cl.
*B32B 15/08* (2006.01)
(52) U.S. Cl. ........................ 428/339; 428/436; 428/437; 428/480
(58) Field of Classification Search ................. 428/436, 428/437, 339, 480
See application file for complete search history.

(56) References Cited

U.S. PATENT DOCUMENTS

| | | |
|---|---|---|
| 2,982,934 A | 5/1961 | Browne |
| 3,893,234 A | 7/1975 | Levin |
| 4,396,826 A | 8/1983 | Orcutt et al. |
| 4,806,432 A | 2/1989 | Eguchi et al. |
| 2004/0033369 A1* | 2/2004 | Fleming et al. ............. 428/431 |
| 2005/0023264 A1 | 2/2005 | Bartrug et al. |

FOREIGN PATENT DOCUMENTS

| | | |
|---|---|---|
| EP | 0 717 459 A1 | 6/1996 |
| GB | 2 125 732 A | 3/1984 |
| JP | 2-219637 A | 9/1990 |
| WO | WO 2004/110747 A1 | 12/2004 |

OTHER PUBLICATIONS

UK Search Report issued in corresponding GB 0520303.9, Dec. 20, 2005, The Patent Office, United Kingdom.

* cited by examiner

*Primary Examiner*—D. S Nakarani
(74) *Attorney, Agent, or Firm*—Buchanan Ingersoll & Rooney PC

(57) ABSTRACT

A laminated glazing comprising two panes of glazing material, a sheet of interlayer material extending therebetween, and an electrically conductive member formed (possibly etched) from a sheet of electrically conductive material also positioned between the panes. The electrically conductive member may function as one or more of: an antenna element, a capacitive sensor, an electromagnetic shield, part of alarm circuitry, a resistance thermometer, a busbar. Also a method of manufacturing such a glazing involving locating a preformed electrically conductive member and a sheet of interlayer material on a first pane of glazing material, placing a second pane of glazing material in register with the first so that the electrically conductive member and the interlayer material are between the two panes, and laminating in an autoclave.

10 Claims, 3 Drawing Sheets

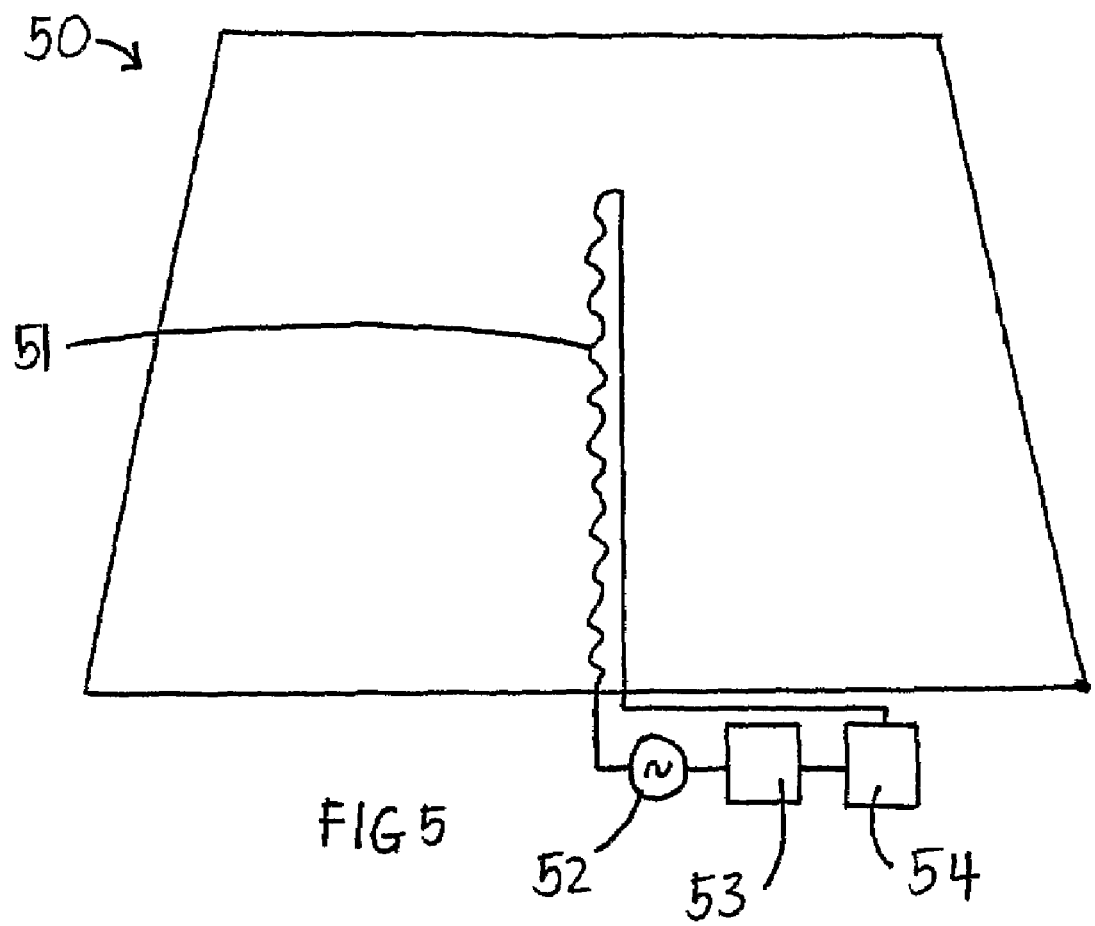

LAMINATED GLAZING

The present invention relates to a laminated glazing, and in particular to a vehicular laminated glazing, which may be used to glaze any opening in a vehicle (for example it may be used as a windshield, a backlight, a sidelight or a rooflight in an automotive vehicle).

A laminated glazing typically comprises two panes of glazing material with a sheet of interlayer material in between. However, further plies of glazing material and interlayer material may be incorporated into a laminate construction as required. Many known laminated glazings have an added functionality, such as being able to transmit and receive electromagnetic radiation via one or more antenna, being able to prevent electromagnetic radiation of a pre-selected wavelength from passing through the glazing by including an electromagnetic shield, and/or including an alarm circuit to detect when one or more of the panes of the laminate have been broken. An antenna may be provided as a metallic button or wire, as a fired silver ink print, or as a metallic coating. An electromagnetic shield may be provided as a coating which selectively blocks radiation of particular wavelengths and which normally extends over the full area of the glazing. An alarm glass may be provided by inclusion of thin wires or a fired silver ink print in a laminate; when the glass is forced, the alarm circuit is activated.

The materials from which each of these functional devices is made include tungsten wires, conductive coatings and fired, silver ink prints. However, each of these materials has associated disadvantages. Tungsten wires can only be laid with a very modest degree of curvature, so that more complex patterns for curved and irregularly shaped glazings cannot be achieved. A conductive coating will often have one or more "hotspots" (areas of localised, increased power density), which typically appear when the area of the coating is non-quadrate (for example if the area of the coating is trapezoidal) or if there are one or more non-heated areas in the coating (which allows radiation that would otherwise be blocked, or at least impeded, by the coating through a glazing). A fired, silver ink print is a visually obtrusive means of including functionality in a laminated glazing, as are copper wires, neither of which is therefore a preferred choice.

The present invention seeks to provide an improved manner of realising the added functionality of a laminated glazing, which does not suffer from the problems set out above. Furthermore, it is desirable that each of the functional devices be realised in the same manner, so that multiple functionality in a glazing may be more easily achieved.

According to the present invention there is provided a laminated glazing comprising
two panes of glazing material,
a sheet of interlayer material extending therebetween, and
an electrically conductive member, also positioned between the panes of glazing material,
wherein the electrically conductive member is formed from a sheet of electrically conductive material.

The sheet of electrically conductive material from which the electrically conductive member is formed is a discrete entity, which exists independently of the other components of the glazing, i.e. it is in the nature of a leaf or foil, as distinct from a layer of deposited material. It is thus quite different from a prior art conductive coating or fired silver ink print, each of which can only exist when formed on a substrate, i.e. a conductive coating and a fired silver ink print cannot exist independently of the pane of glazing material on which they are deposited. The sheet of electrically conductive material may ordinarily have a thickness less than 200 μm because at any greater thickness the sheet may be difficult to process for inclusion in the glazing, and preferably between 5 and 15 μm. For the avoidance of doubt, "thickness" refers to the depth of the material in a direction perpendicular to the glazing. Wires typically have a diameter in the range 0.025 to 0.15 mm, and so are much thicker and more visually obtrusive than an electrically conductive member made from a sheet of electrically conductive material.

The panes of glazing material may be panes of glass, one or both of which may be clear or tinted, and which may also be toughened, or panes of a plastics material, for example polycarbonate. The panes of glazing material may be flat or they may be curved. Each pane of glazing material may be between 0.5 and 25 mm in thickness, preferably between 1 and 5 mm. The sheet of interlayer material may be any material known in the art that is suitable for joining two panes of glazing material together to form a laminate. Preferably, the interlayer material is polyvinylbutyral ("PVB") and it typically provided in a thickness of between 0.38 and 1.1 mm, but most commonly 0.76 mm. The overall thickness of the laminated glazing may therefore be between 2 and 100 mm, and preferably between 3 and 6 mm.

Preferably the electrically conductive member is etched from the sheet of electrically conductive material. More preferably, the member is photochemically-etched from the sheet of material. One method of photochemical etching that may be used to form the electrically conductive member involves creating a template of the member, placing the template over a sheet of electrically conductive material which has been surface treated with a photo-sensitive lacquer, subjecting this duplet to radiation so that the exposed portions of the lacquer are photochemically degraded, and using an acid to remove the degraded lacquer and the corresponding areas of the electrically conductive material below. However, any other etching procedure known in the art which could form the electrically conductive member would be suitable.

The electrically conductive member may function as one or more of the following:
  a) an antenna element
  b) a capacitive sensor
  c) an electromagnetic shield
  d) part of alarm circuitry
  e) a resistance thermometer
  f) a busbar The antenna element may comprise one or more antenna. The antenna may be designed to have a size, shape and configuration as is known in the art, to receive and transmit electromagnetic radiation for the following applications: a mobile telephone, a global positioning system ("GPS"), television, radio (AM, FM, digital), and the like. To perform the function of an antenna element the electrically conductive member must be connectable by a suitable connection means (for example a co-axial cable) to the device in question (mobile phone, radio, etc.). Other electronic components such as an amplifier may be connectable between the antenna element and the device.

A capacitive sensor may be created in the glazing by providing that the glazing, and hence the electrically conductive member, forms part of an electrical circuit (which is incomplete when the glazing is stand-alone and not yet fitted into, for example, a vehicle). To create such a circuit the following components are usually required: an electrical power source (for example a vehicle battery), a meter for measuring the capacitance of the circuit, a first electrical conductor external of the glazing (for example the bodywork of a vehicle) and wiring to connect these elements together and to the electrically conductive member.

Electrical current (preferably AC) may be supplied to the circuit, and by considering the flow in one direction only for the purposes of the following explanation, it may be supplied to the electrically conductive member (but can go no further until the circuit is completed). When a second external electrical conductor (usually in the form of a human being) approaches (or makes contact with) the glazing, the current capacitively flows from the electrically conductive member in the glazing to and through the second external electrical conductor, then onto the first external electrical conductor (again capacitively) and finally back to the current source to complete the circuit. The meter may be connected in series between the first external electrical conductor and the current source where it may detect the presence of the second electrical conductor.

A capacitive sensor may function as a rain sensor, especially when the glazing is a vehicle glazing, and preferably when it is a windscreen or backlight. A rain sensor is normally supplied with a vehicle glazing to automatically activate the wipers on the vehicle when a threshold level of "rain" has been detected. This additional functionality may be achieved by including suitable wiper-activation electronics within the electrical circuit.

An electromagnetic shield may be provided by forming a mesh out of the sheet of electrically conductive material. Typically the mesh may be provided over the entire area of the glazing. The spacings in the mesh may be chosen to correspond with the wavelength of the radiation that is sought to be shielded. When the glazing is installed in a vehicle, the shield may be connected to the metallic bodywork of the vehicle so as to enhance the shielding properties that the vehicle already possesses (i.e. the Faraday cage effectively created by the vehicle bodywork may be extended by the presence of one or more shielding glazings in the window apertures of the vehicle).

Alarm circuitry, for which a glazing comprising an electrically conductive member may form a part, is known in the art and generally includes alarm-activating electronics, a current source to provide electrical current to flow around the alarm circuit and an alarm output (for example, a horn, flashing light, etc.). The design of the electrically conductive member inside the glazing preferably is such that is covers the entire glazing, thus a breakage anywhere in the glazing may trigger the alarm (once the glazing has been suitably connected into the alarm circuitry).

The electrically conductive member may function as a resistance thermometer when the glazing is connected to suitable resistance measuring equipment. Essentially the resistance over the area of the electrically conductive material may be measured and compared to known measurements at different temperatures for the material (and the area of it) in question. The measuring and comparing equipment may be connected to an output which would display the temperature of the glazing.

Preferably the electrically conductive member is black in colour, to minimise its appearance in the glazing; the black colouration may be achieved by oxidation of the member.

To perform its function, the electrically conductive member may require a supply of electrical energy, as discussed earlier. A pair of busbars may be provided to supply an electric current to the electrically conductive member. The busbars may exist independently of the electrically conductive member and may be made from, for example, tinned copper strips or silver prints, as is known. However, the busbars may also be formed from a sheet of electrically conductive material, in the same manner as the electrically conductive member itself. For simplicity of assembly of the glazing, the electrically conductive member may comprise the pair of busbars, such that the member and the associated busbars are formed as one continuous piece from the sheet of electrically conductive material.

The electrically conductive member may itself be provided on a sheet of polymeric material. Any sheet of polymeric material suitable for including in a laminate may be used, however polyethylene terephthalate ("PET") is preferred because at the lamination temperatures used, it is a relatively stable material, it is transparent and it is readily available. When incorporated into the laminated glazing, the sheet of polymeric material and the electrically conductive member may themselves be laminated between two plies of interlayer material, forming a composite interlayer (which is then laminated between the two panes of glazing material).

The laminated glazing may be curved, in which case, the composite interlayer may be pre-formed and pre-shaped to have the curvature of the final glazing. One way in which the composite interlayer may be pre-shaped is described in WO 2004/110747 A1, where a thermoplastic functional film is thermoformed and subsequently cooled by forced draught prior to its introduction between the panes which are to form a laminate.

Preferably the sheet of polymeric material has a thickness less than 1 mm, and further preferably between 0.05 and 0.20 mm. The composite interlayer may therefore usually have a thickness less than 1.6 mm, and more typically between 0.76 and 1 mm.

The surface area of the electrically conductive member may vary in relation to the dimensions of the laminated glazing of which it is a part, so that it may extend over only a small area of the glazing (approximately 10%) or a larger area of the glazing (approximately 80%). Preferably, however the electrically conductive member is substantially co-extensive with the sheet of interlayer material (or the composite interlayer, where appropriate) and the panes of glazing material. By "substantially co-extensive" is meant that the electrically conductive member extends over the entire surface area of the glazing itself. The reason for avoiding the area around the periphery of the glazing is to prevent corrosion of the member which may occur if it is located too close to the environment external of the glazing.

When the laminated glazing is used as an automotive vehicle glazing, one or more panes of the glazing may be provided with an obscuration band (typically an opaque band which masks the interface between the glazing and the vehicle and which shields the adhesive that holds the glazing in place from damaging ultra-violet radiation), which may extend around the entire periphery of the glazing. The obscuration band may be provided with a fade out band (a continuation of the obscuration band but having the obscuration applied in a decorative pattern over from 1 to 99% of the remaining surface area of the glazing) which extends inwardly therefrom. When the electrically conductive member is substantially co-extensive with the remainder of the glazing (as described above) the outer extremity of the electrically conductive member may lie within the fade out band, thereby hiding the extremity from view—this may be done in accordance with EP 1 135 252 B1. The electrically conductive member may comprise a metal selected from a group which includes copper, silver, gold, and aluminium or a metal alloy (e.g. iron nickel or steel).

According to the present invention there is also provided a method of manufacturing a laminated glazing as hereinbefore described comprising a) forming an electrically conductive member from a sheet of electrically conductive material, b) locating the electrically conductive member and a sheet of interlayer material on a first pane of glazing material, c) positioning a second pane of glazing material in register with the first pane of glazing material so that the electrically conductive member and the sheet of interlayer material are between the first and second panes, and d) laminating the glazing in an autoclave.

The electrically conductive member is preferably etched from the sheet of electrically conductive material, as described earlier. The electrically conductive member may be supplied on a sheet of polymeric material, which may be interleaved between two sheets of interlayer material to form a composite interlayer, when in then located on the first pane of glazing material.

The laminated glazing may be curved. When this is the case, the composite interlayer may be pre-shaped to the curvature of the glazing prior to it being incorporated into the glazing, again as described earlier.

For a better understanding, the present invention will now be more particularly described by way of non-limiting example with reference to, and as shown in, the accompanying schematic drawings wherein:

FIG. 5 is a plan view of a laminated glazing according to the fifth embodiment of the invention.

Figure 1:
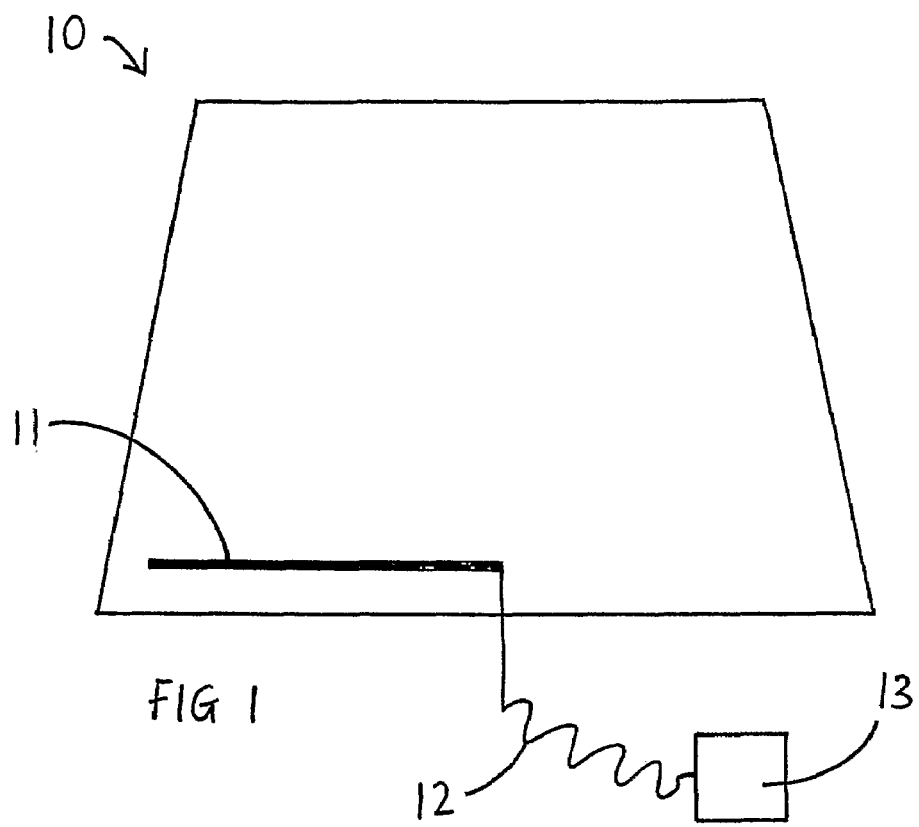
FIG. 1 is a plan view of a laminated glazing according to a first embodiment of the invention.

FIG. 1 illustrates laminated glazing 10, in the form of a vehicle windscreen, which comprises electrically conductive member 11, in the form of an antenna element, connected to device 13, in the form of a mobile telephone, via connections means 12, in the form of a co-axial cable. Although not shown, laminated glazing 10 further comprises an outer pane of glazing material and inner pane of glazing material, each in the form of a ply of soda-lime-silica glass. The terms "outer" and "inner" refer to the orientation of glazing 10 when installed in a vehicle. Laminated between the outer and inner panes of glazing material is a composite interlayer. The composite interlayer comprises a ply of polymeric material, in the form of a ply of PET, interleaved between two plies of interlayer material, in the form of plies of PVB. Electrically conductive member 11 is provided on the ply of polymeric material.

Figure 2:
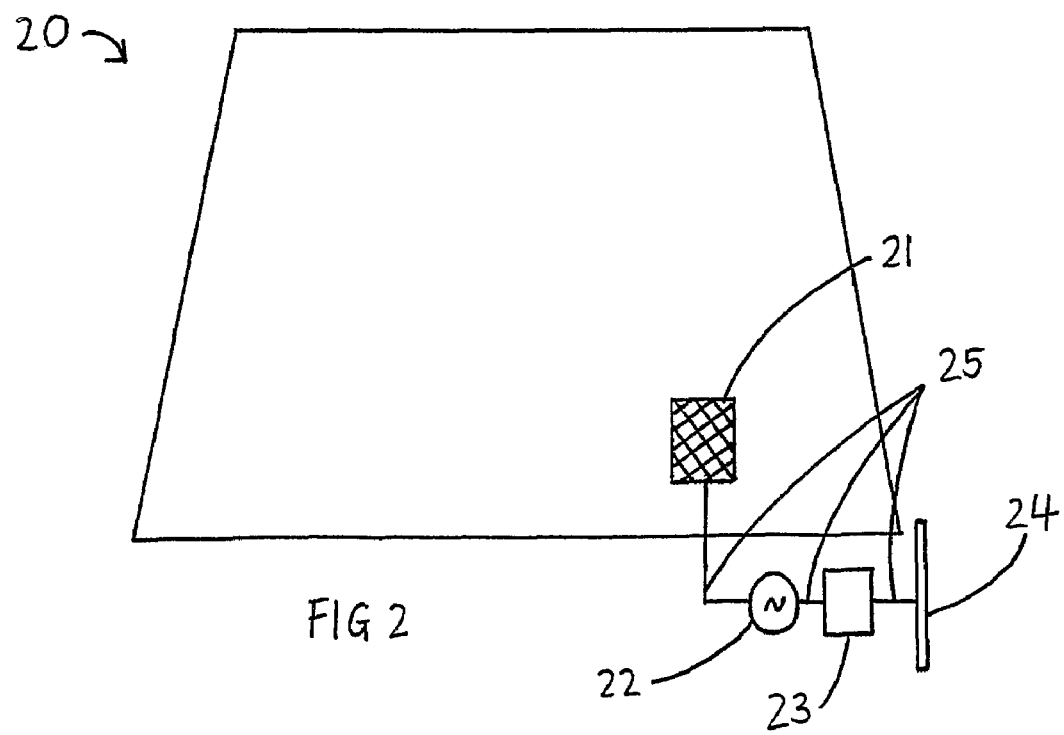
FIG. 2 is a plan view of a laminated glazing according to a second embodiment of the invention.

FIG. 2 shows laminated glazing 20, in the form of a vehicle windscreen, which comprises electrically conductive member 21, in the form of a capacitive plate which is a small meshed area of electrically conductive material, connected in series to power source 22, for example a vehicle battery, and first external conductor 24, for example vehicle bodywork, via connection means 25, in the form of standard wiring. Meter 23 for measuring the capacitance of the completed circuit is connected in series between power source 22 and first external conductor 24. The circuit is completed by a second external conductor (not shown), usually in the form of a human being, approaching first external conductor 24 and also electrically conductive member 21; electrical current flows (capacitively where necessary) around the circuit and the capacitance measured by meter 23. Additional electronics which act on the detected capacitance of the circuit, for example to activate wiper blades, may also be incorporated into the circuit.

Figure 3:
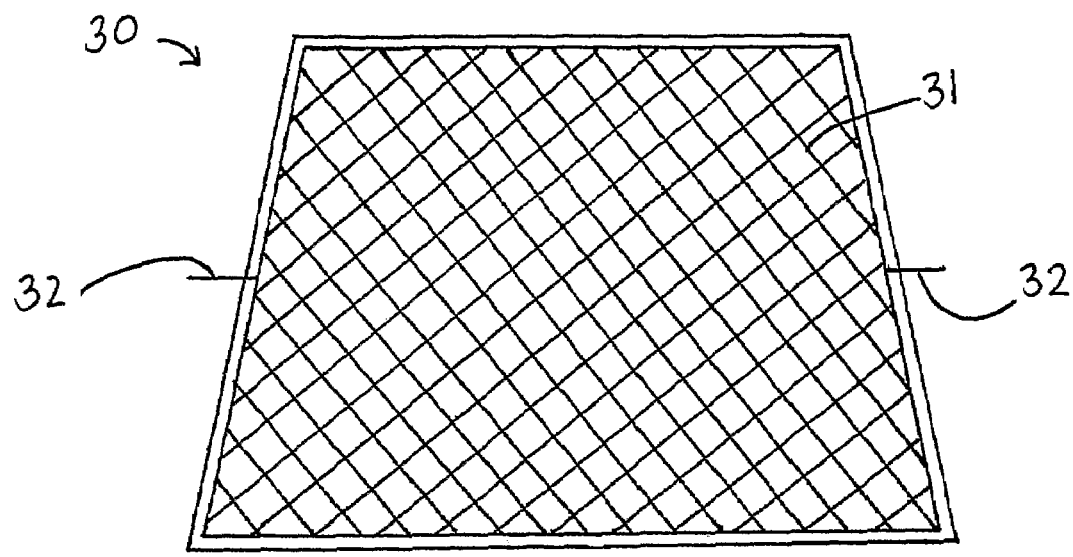
FIG. 3 is a plan view of a laminated glazing according to a third embodiment of the invention.

FIG. 3 shows laminated glazing 30, in the form of a vehicle windscreen, comprising electrically conductive member 31, in the form of electromagnetic shield for blocking electromagnetic radiation of a certain, pre-determined wavelength (i.e. the size of the holes in the mesh have been pre-selected for the wavelength that is sought to be blocked). Electrically conductive member 31 comprises extensions 32 which may be used to connect member 31 to the bodywork of a vehicle to provide metallic continuity and shielding from external radiation.

Figure 4:
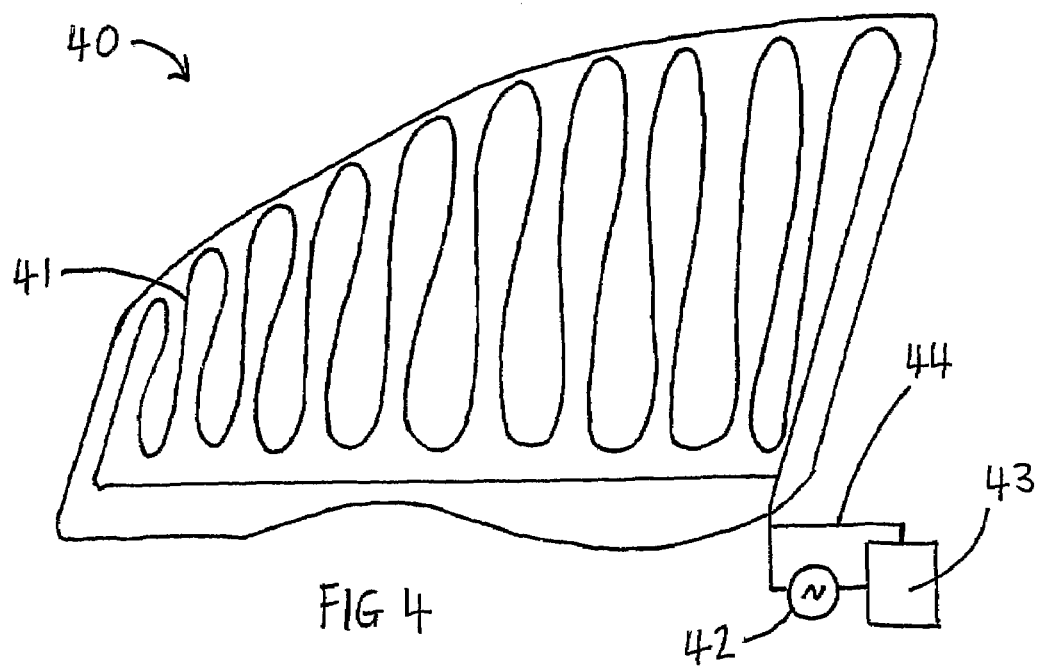
FIG. 4 is a plan view of a laminated glazing according to the fourth embodiment of the invention.

FIG. 4 illustrates laminated glazing 40, in the form of a vehicle windscreen, which comprises electrically conductive member 41, in the form of alarm line, connected in series to power source 42, for example a vehicle battery, and alarm-activating electronics and output 42, via connection means 44, in the form of standard wiring. When glazing 40 is broken, electrically conductive member 41 is compromised and hence the alarm circuit is broken; alarm-activating electronics and output 42 detects the broken circuit and activates the alarm.

FIG. 5 depicts laminated glazing 50, in the form of a vehicle windscreen, comprising electrically conductive member 51, in the form of resistance thermometer line, connected in series to power source 52, for example a vehicle battery, resistance measurer and comparer 53 and temperature output 54. Power is supplied to electrically conductive member 51, whose resistance is temperature dependent. Resistance measurer and comparer 53 measures the resistance of member 51 and compare this resistance to known temperatures for the material used. The temperature is then displayed on output 54.

Each of the glazings in FIGS. 2 to 5 have a construction that is similar to that of glazing 1 described earlier, in that each comprises a composite interlayer (a ply of PET and two plies of PVB) which is interleaved between panes of soda-lime-silica glass. The electrically conductive member which features in all of the glazings shown in FIGS. 1 through to 5 may be an etched sheet of copper foil, or other such suitable etched conductive medium, such as a foil of silver, gold, aluminium, an iron-nickel alloy or a steel. Etched conductive sheets are currently available from Scheuten Precision Technologies, Nusterweg 66, NL-6136 XB Sittard, Netherlands (website: www.mptec.biz).

The invention claimed is:

1. A laminated glazing comprising
two panes of glazing material,
a sheet of interlayer material extending therebetween, and
an electrically conductive member, also positioned between the panes of glazing material, wherein the electrically conductive member is formed from a sheet of electrically conductive material and functions as one or more of the following:
a) an antenna element,
b) a capacitive sensor,
c) an electromagnetic shield,
d) part of alarm circuitry,
e) a resistance thermometer,
wherein the electrically conductive member is etched from the sheet of electrically conductive material.

2. A laminated glazing as claimed in claim 1 wherein the electrically conductive member as a capacitive sensor functions as a rain sensor.

3. A laminated glazing as claimed in claim 1 wherein the electrically conductive member is provided on a sheet of polymeric material.

4. A laminated glazing as claimed in claim 3 wherein the polymeric material is polyethylene terephthalate.

5. A laminated glazing as claimed in claim 3 wherein the sheet of polymeric material and the electrically conductive member are themselves laminated between two plies of interlayer material forming a composite interlayer.

6. A laminated glazing as claimed in claim 5 wherein the glazing is curved and the composite interlayer is pre-formed and pre-shaped to have the curvature of the glazing.

7. A laminated glazing as claimed in claim 5 wherein the composite interlayer has a thickness less than 1.6 mm.

8. A laminated glazing as claimed in claim 3 wherein the sheet of polymeric material has a thickness less than 1 mm.

9. A laminated glazing as claimed in claim 8 wherein the electrically conductive member is substantially co-extensive with the sheet of interlayer material and the panes of glazing material.

10. A laminated glazing as claimed in claim 9 wherein the electrically conductive member comprises a metal selected from a group which includes copper, silver, gold and aluminum or a metal alloy.

* * * * *